(12) United States Patent
Patterson et al.

(10) Patent No.: US 9,314,337 B2
(45) Date of Patent: *Apr. 19, 2016

(54) MICROSTRUCTURED IMPLANT SURFACES

(71) Applicant: Titan Spine, LLC, Mequon, WI (US)

(72) Inventors: Chad J. Patterson, Port Washington, WI (US); Jennifer M. Schneider, Germantown, WI (US); Peter F. Ullrich, Jr., Neenah, WI (US); Mark E. Berg, Mequon, WI (US)

(73) Assignee: Titan Spine, LLC, Mequon, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/644,274

(22) Filed: Mar. 11, 2015

(65) Prior Publication Data
US 2015/0202047 A1 Jul. 23, 2015

Related U.S. Application Data

(63) Continuation of application No. 13/286,813, filed on Nov. 1, 2011, now Pat. No. 8,992,619.

(51) Int. Cl.
*A61F 2/44* (2006.01)
*A61F 2/30* (2006.01)
(Continued)

(52) U.S. Cl.
CPC ............ *A61F 2/30767* (2013.01); *A61F 2/4455* (2013.01); *A61F 2/4465* (2013.01); *A61F 2/4611* (2013.01); *A61F 2002/2817* (2013.01); *A61F 2002/2835* (2013.01); *A61F 2002/30013* (2013.01); *A61F 2002/3084* (2013.01);
(Continued)

(58) Field of Classification Search
CPC ....... A61F 2/44; A61F 2/4455; A61F 2/4465; A61F 2/4611; A61F 2002/30838; A61F 2002/3084
USPC ........................................... 623/17.11, 17.16
See application file for complete search history.

(56) References Cited

U.S. PATENT DOCUMENTS 7,018,418 B2 3/2006 Amrich et al.
7,662,186 B2 2/2010 Bagga et al.
(Continued)

FOREIGN PATENT DOCUMENTS

WO 9706753 2/1997
WO 98/01091 1/1998
(Continued)

OTHER PUBLICATIONS

Astra Tech Dental, "Nanolevel topographic modifications on the OsseoSpeed surface", http://shop.dentsplyimplants.us, Mar. 8, 2001.
(Continued)

*Primary Examiner* — Nicholas Plionis
(74) *Attorney, Agent, or Firm* — Stradley Ronon Stevens & Young, LLP

(57) ABSTRACT

An implantable device for treating disc degenerative disease and arthritis of the spine. The implant is sized for placement into an intravertebral disc space. The implant has a body with a predetermined, defined, repeating, three-dimensional pattern at least partially on at least one of its surfaces. The pattern is adapted to create a surface area of bone-contacting features that enhance in-growth and biological attachment to a biocompatible material. Also disclosed are process steps for making the implant.

18 Claims, 13 Drawing Sheets

(51) Int. Cl.
*A61F 2/46* (2006.01)
*A61F 2/28* (2006.01)

(52) U.S. Cl.
CPC . *A61F2002/3092* (2013.01); *A61F 2002/3093* (2013.01); *A61F 2002/3097* (2013.01); *A61F 2002/30321* (2013.01); *A61F 2002/30454* (2013.01); *A61F 2002/30769* (2013.01); *A61F 2002/30774* (2013.01); *A61F 2002/30779* (2013.01); *A61F 2002/30785* (2013.01); *A61F 2002/30787* (2013.01); *A61F 2002/30789* (2013.01); *A61F 2002/30838* (2013.01); *A61F 2002/30906* (2013.01); *A61F 2002/30925* (2013.01); *A61F 2002/30927* (2013.01); *A61F 2002/30985* (2013.01); *A61F 2002/4475* (2013.01); *A61F 2002/4629* (2013.01); *A61F 2310/00023* (2013.01); *A61F 2310/00407* (2013.01); *Y10S 977/81* (2013.01); *Y10S 977/91* (2013.01)

(56) References Cited

U.S. PATENT DOCUMENTS

| | | |
|---|---|---|
| 8,262,737 B2 | 9/2012 | Bagga et al. |
| 2003/0181980 A1 | 9/2003 | Berry et al. |
| 2003/0181981 A1 | 9/2003 | Lemaire |
| 2003/0187506 A1 | 10/2003 | Ross et al. |
| 2003/0191531 A1 | 10/2003 | Berry et al. |
| 2004/0073314 A1 | 4/2004 | White et al. |
| 2004/0117019 A1 | 6/2004 | Trieu et al. |
| 2004/0117020 A1 | 6/2004 | Frey et al. |
| 2004/0122518 A1 | 6/2004 | Rhoda |
| 2004/0127993 A1 | 7/2004 | Kast et al. |
| 2004/0153154 A1 | 8/2004 | Dinkelacker |
| 2004/0153160 A1 | 8/2004 | Carrasco |
| 2004/0162616 A1 | 8/2004 | Simonton et al. |
| 2004/0167632 A1 | 8/2004 | Wen et al. |
| 2004/0210309 A1 | 10/2004 | Denzer et al. |
| 2004/0230306 A1 | 11/2004 | Hoeck et al. |
| 2004/0265780 A1 | 12/2004 | Robb et al. |
| 2004/0267367 A1 | 12/2004 | O'Neil |
| 2005/0021150 A1 | 1/2005 | Michelson |
| 2005/0027360 A1 | 2/2005 | Webb et al. |
| 2005/0038512 A1 | 2/2005 | Michelson |
| 2005/0060034 A1 | 3/2005 | Berry et al. |
| 2005/0075734 A1 | 4/2005 | Fulton et al. |
| 2005/0085913 A1 | 4/2005 | Fraser et al. |
| 2005/0131416 A1 | 6/2005 | Jansen et al. |
| 2005/0147942 A1 | 7/2005 | Hall |
| 2005/0159814 A1 | 7/2005 | Karahalios |
| 2005/0161120 A1 | 7/2005 | Inagaki et al. |
| 2005/0165483 A1 | 7/2005 | Ray et al. |
| 2005/0203630 A1* | 9/2005 | Pope et al. ............... 623/20.21 |
| 2005/0251257 A1 | 11/2005 | Mitchell et al. |
| 2006/0041313 A1 | 2/2006 | Allard et al. |
| 2006/0093646 A1 | 5/2006 | Cima et al. |
| 2006/0100705 A1 | 5/2006 | Puno et al. |
| 2006/0149372 A1 | 7/2006 | Paxson et al. |
| 2006/0149376 A1 | 7/2006 | Shimp et al. |
| 2006/0167549 A1 | 7/2006 | Mathys, Jr. et al. |
| 2006/0190079 A1 | 8/2006 | Istephanous et al. |
| 2006/0219661 A1 | 10/2006 | Towse et al. |
| 2006/0235534 A1 | 10/2006 | Gertzman et al. |
| 2006/0265065 A1 | 11/2006 | Bagga et al. |
| 2006/0293748 A1 | 12/2006 | Alexander et al. |
| 2007/0010885 A1 | 1/2007 | Liu et al. |
| 2007/0093898 A1 | 4/2007 | Schwab et al. |
| 2007/0118220 A1 | 5/2007 | Liu et al. |
| 2007/0118223 A1 | 5/2007 | Allard et al. |
| 2007/0233247 A1 | 10/2007 | Schwab |
| 2007/0233248 A1 | 10/2007 | Schwab et al. |
| 2007/0260320 A1 | 11/2007 | Peterman et al. |
| 2007/0269475 A1 | 11/2007 | Gil et al. |
| 2007/0270951 A1 | 11/2007 | Davis et al. |
| 2007/0270956 A1 | 11/2007 | Heinz |
| 2007/0282441 A1 | 12/2007 | Stream et al. |
| 2007/0288028 A1 | 12/2007 | Gorensek et al. |
| 2007/0293949 A1 | 12/2007 | Salerni et al. |
| 2008/0014243 A1 | 1/2008 | Ellingsen et al. |
| 2008/0071380 A1 | 3/2008 | Sweeney |
| 2008/0077171 A1 | 3/2008 | Blain et al. |
| 2008/0097610 A1 | 4/2008 | Guyer et al. |
| 2008/0154378 A1 | 6/2008 | Pelo |
| 2008/0195209 A1 | 8/2008 | Garcia et al. |
| 2008/0221689 A1 | 9/2008 | Chaput et al. |
| 2008/0249622 A1 | 10/2008 | Gray |
| 2008/0262623 A1 | 10/2008 | Bagga et al. |
| 2008/0269764 A1 | 10/2008 | Blain et al. |
| 2008/0269806 A1 | 10/2008 | Zhang et al. |
| 2008/0288076 A1 | 11/2008 | Soo et al. |
| 2009/0005784 A1 | 1/2009 | Blain et al. |
| 2009/0005871 A1 | 1/2009 | White et al. |
| 2009/0014243 A1 | 1/2009 | Whingham |
| 2009/0024132 A1 | 1/2009 | Blain et al. |
| 2009/0082819 A1 | 3/2009 | Blain et al. |
| 2009/0088800 A1 | 4/2009 | Blain et al. |
| 2009/0088853 A1 | 4/2009 | Ogilvie et al. |
| 2009/0132048 A1 | 5/2009 | Denzer |
| 2009/0182432 A1 | 7/2009 | Zdeblick et al. |
| 2009/0187247 A1 | 7/2009 | Metcalf, Jr. et al. |
| 2009/0204152 A1 | 8/2009 | Blain |
| 2009/0234362 A1 | 9/2009 | Blain et al. |
| 2009/0264928 A1 | 10/2009 | Blain |
| 2009/0276049 A1 | 11/2009 | Weiland |
| 2009/0312837 A1 | 12/2009 | Eisermann et al. |
| 2010/0121385 A1 | 5/2010 | Blain et al. |
| 2010/0173264 A1 | 7/2010 | Fredriksson et al. |
| 2010/0204798 A1 | 8/2010 | Gerbec et al. |
| 2010/0218854 A1 | 9/2010 | Garcia Saban et al. |
| 2010/0228288 A1 | 9/2010 | Blain |
| 2010/0249937 A1 | 9/2010 | Blain et al. |
| 2010/0274286 A1 | 10/2010 | Blain et al. |
| 2010/0274358 A1 | 10/2010 | Mueller et al. |
| 2010/0303722 A1 | 12/2010 | Jin et al. |
| 2011/0009965 A1 | 1/2011 | Ankem |
| 2011/0040301 A1 | 2/2011 | Blain et al. |
| 2011/0082503 A1 | 4/2011 | Blain |
| 2011/0190902 A1 | 8/2011 | Tong et al. |
| 2011/0224796 A1 | 9/2011 | Weiland et al. |
| 2011/0230970 A1 | 9/2011 | Lynn et al. |
| 2011/0233169 A1 | 9/2011 | Mayfield et al. |
| 2011/0282454 A1 | 11/2011 | Ullrich, Jr. et al. |
| 2012/0009341 A1 | 1/2012 | Noh et al. |
| 2012/0046695 A9 | 2/2012 | Blain |
| 2012/0123424 A1 | 5/2012 | Blain et al. |
| 2012/0123548 A1 | 5/2012 | Lynn et al. |
| 2012/0136443 A1 | 5/2012 | Wentzel |
| 2012/0149991 A1 | 6/2012 | Blain et al. |
| 2012/0158056 A1 | 6/2012 | Blain |
| 2012/0158144 A1 | 6/2012 | Ullrich, Jr. et al. |
| 2012/0172991 A1 | 7/2012 | Bertele et al. |
| 2012/0232664 A1 | 9/2012 | Ulrich, Jr. et al. |
| 2012/0239150 A1 | 9/2012 | Ullrich, Jr. et al. |
| 2012/0239151 A1 | 9/2012 | Ullrich, Jr. et al. |
| 2012/0239152 A1 | 9/2012 | Ullrich, Jr. et al. |
| 2012/0239153 A1 | 9/2012 | Ullrich, Jr. et al. |
| 2012/0239154 A1 | 9/2012 | Ullrich, Jr. et al. |
| 2012/0245694 A1 | 9/2012 | Ullrich, Jr. et al. |
| 2012/0277876 A1 | 11/2012 | Ullrich, Jr. et al. |
| 2012/0303127 A1 | 11/2012 | Ullrich, Jr. et al. |
| 2012/0303128 A1 | 11/2012 | Ullrich, Jr. et al. |
| 2012/0303129 A1 | 11/2012 | Bagga et al. |
| 2012/0310354 A1 | 12/2012 | Ullrich, Jr. et al. |
| 2012/0312778 A1 | 12/2012 | Ullrich, Jr. et al. |
| 2012/0312779 A1 | 12/2012 | Patterson et al. |
| 2012/0316650 A1 | 12/2012 | Ullrich, Jr. et al. |
| 2012/0316651 A1 | 12/2012 | Ullrich, Jr. et al. |

(56) References Cited

U.S. PATENT DOCUMENTS

| | | |
|---|---|---|
| 2012/0316653 A1 | 12/2012 | Ullrich, Jr. et al. |
| 2013/0006363 A1 | 1/2013 | Ullrich, Jr. et al. |

FOREIGN PATENT DOCUMENTS

| | | |
|---|---|---|
| WO | 9801091 | 1/1998 |
| WO | 0128469 | 4/2001 |
| WO | 0170144 | 9/2001 |
| WO | 0195838 | 12/2001 |
| WO | 2004041131 | 5/2004 |
| WO | 2006081843 | 8/2006 |
| WO | 2006116306 | 11/2006 |
| WO | 2006119088 | 11/2006 |
| WO | 2006121795 | 11/2006 |
| WO | 2007089905 | 8/2007 |
| WO | 2008103843 | 8/2008 |
| WO | 2009006225 | 1/2009 |
| WO | 2009029458 | 3/2009 |
| WO | 2009129262 | 10/2009 |
| WO | 2009140544 | 11/2009 |

OTHER PUBLICATIONS

Astra Tech Dental, "OsseoSpeed—more bone more rapidly", http://shop.dentsplyimplants.us, May 2011.

Guo, et al., "The effect of hydrofluoric acid treatment of TiO2 grit blasted titanium implants on adherent osteoblast gene expression in vitro and in vivo", Biomaterials 28 (Sep. 14, 2007) 5418-5425.

He, et al., "Mechanical and Histomorphometric Evaluations of Rough Titanium Implants Treated with Hydrofluoric Acid/Nitric Acid Solution in Rabbit Tibia", Int. J. Oral Maxillofac. Implants, Nov. 1, 2011; 26:115-122.

Isa, et al., "Effects of Fluoride-Modified Titanium Surfaces on Osteoblast Proliferation and Gene Expression", Int. J. Oral Maxillofac. Implants 2006; 21:203-211.

Lamolle, et al., "The effect of hydrofluoric acid treatment of titanium surface on nanostructural and chemical changes and the growth of MC3T3-E1 cells", Biomaterials 30 (Nov. 20, 2008) 736-742.

Meirelles, et al., "The Effect of Chemical and Nanotopographical Modifications on the Early Stages of Osseointegration", Int. J. Oral Maxillofac. Implants 2008; 23:641-647.

Supplementary Partial European Search Report issued Sep. 27, 2011.

Supplementary Partial European Search Report issued Aug. 19, 2011.

Variola, et al., "Nanoscale surface modifications of medically relevant metals: state-of-the art and prespectives", Nanoscale, 2011, 3, 335-353.

Wennerberg, et al., "Spontaneously formed nanostructures on titanium surfaces", Clin. Oral Impl. Res., 2012, 1-7.

\* cited by examiner

Confocal laser mircoscopy images and average-roughness ($S_a$) values of PEEK (A), sTiAlV (B), and rTiAlV (C) surfaces. of 644 × 644 μm² field,

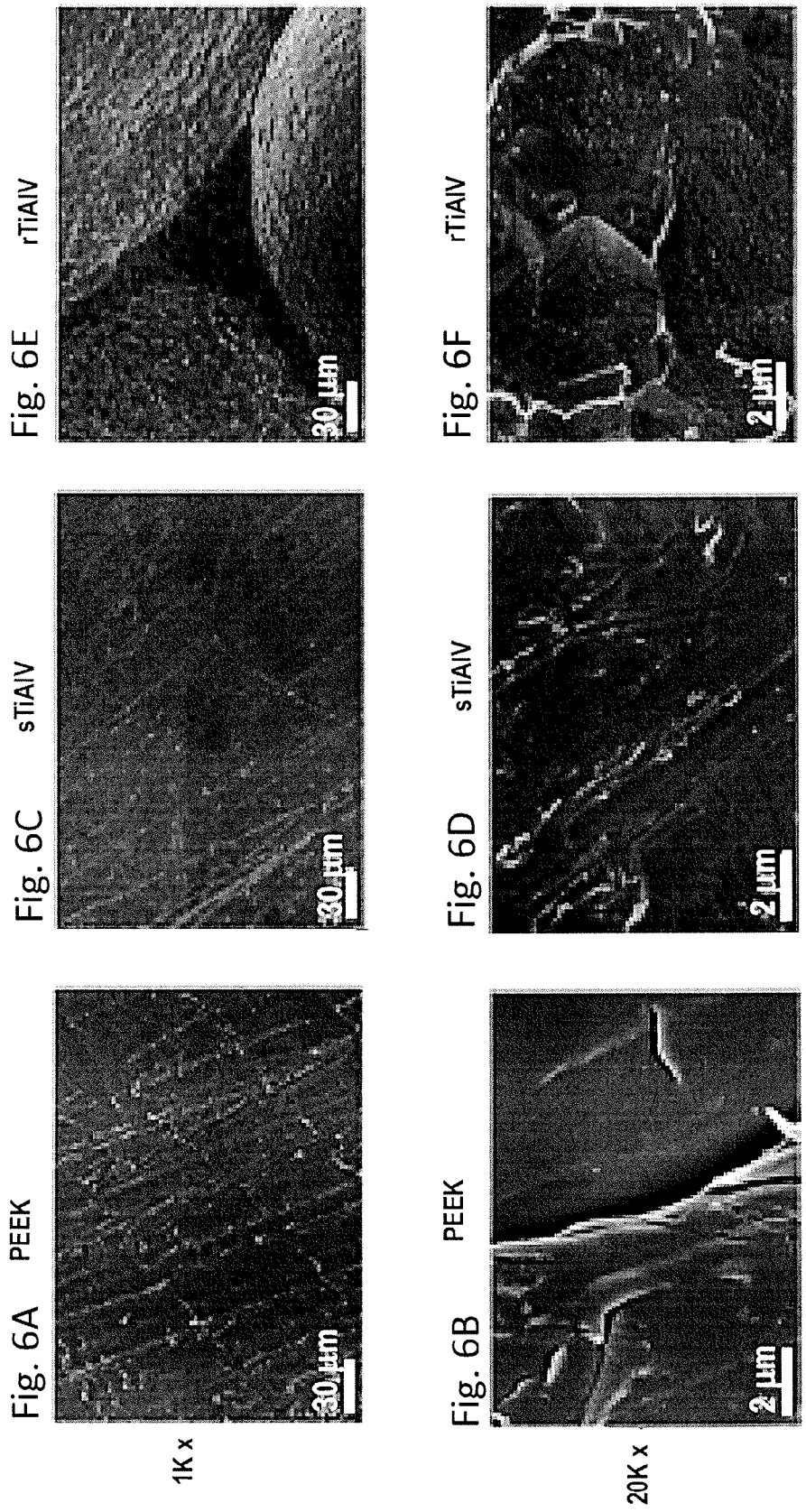
SEM images of PEEK (A, B), sTiAlV (C, D), and rTiAlV (E, F) surfaces at low and high magnifications.

DETAIL Ma
SCALE 40 : 1

Results of Osteogenic Markers

Cytokine Analysis - BMP and TGFβ

MICROSTRUCTURED IMPLANT SURFACES

RELATED APPLICATION

This application is a continuation U.S. patent application Ser. No. 13/286,813 filed on Nov. 1, 2011, the contents of which are incorporated in this application by reference in their entirety and for all purposes.

TECHNICAL FIELD

The present invention relates to microstructured medical implant surfaces, and to processes for producing such surfaces. This invention also relates generally to the treatment of disc degenerative disease or arthritis of the spine and to spinal implants having microstructured surfaces used to treat such conditions.

BACKGROUND OF THE INVENTION

In the simplest terms, the spine is a column made of vertebrae and discs. The vertebrae provide the support and structure of the spine while the spinal discs, located between the vertebrae, act as cushions or "shock absorbers." These discs also contribute to the flexibility and motion of the spinal column. FIG. 1A (described in greater detail below) shows a perspective view of a healthy vertebral column including a disc separating vertebrae.

Over time, the discs may become diseased or infected, develop deformities such as tears or cracks, or simply lose structural integrity, for example discs may bulge or flatten. These impaired discs can affect the anatomical functions of the vertebrae, due to the resultant lack of proper biomechanical support, and are often associated with chronic back pain. FIG. 1B (also described in greater detail below) shows a perspective view of a vertebral column including a damaged disc and vertebrae.

Disc degeneration may occur as part of the normal aging process or as a result of traumatic injury to the soft and flexible disc positioned between the vertebrae. The resulting structural collapse under load may cause, among other things, significant pain and loss of motion. Due to these conditions, other health issues may result.

Where the goal of the treatment of such health issues is to rigidly fix individual spinal vertebra after the surgical removal of damaged or diseased disc tissues, the engagement and subsequent integration of implant surfaces in contact with the vertebral bone is required. Rigid fixation helps to enhance immediate recovery from surgery and helps both in the early stages of healing and over the longer term. Loads through daily activities over the longer term are shared between the implanted device, or implant, and the resulting osseous (i.e., comprised of, containing, or resembling bone) growth in and around the device.

Some implants are treated using various methods, including coatings, etching processes utilizing chemicals, and acids resulting in roughened or prepared surfaces that enhance bone in-growth. See, for example, U.S. Pat. Nos. 5,876,453, 5,258,098, 6,923,810 to Michelson and U.S. Pat. No. 7,311,734 to Van Hoeck et al., each of which is incorporated by reference herein. The patterns generated in these processes are often intentionally random and irregular. Many acid-etched surfaces on implant devices, for example, are random and irregular due to the application of masking materials in an intentionally random manner. These surfaces are not optimum because they are inconsistent between devices and are difficult to manufacture with precision and repeatability. Patterned surfaces also typically may have only one depth from the original surface and as a result the depth can have too deep a feature that in effect raises stresses between the bone and implants. By using multiple cuts of a predetermined depth and overlapping at a designed interval the overall effect of improved stability is balanced against over stressing the osseos interface.

Because bone tissues are organic and irregular in their growth patterns, the tissues will adhere in an irregular manner regardless of the surface pattern or orientation. This adherence is often sufficient for the initial stabilization, but not necessarily the most efficient way to prevent movement in the critical early healing phases after implantation. Long-term bone in-growth does not necessarily benefit from the irregular patterns, but is not necessarily hindered by it either.

The stimulation of bone growth through specific patterns include textures and roughness in the macro, micron/submicron and nano sized range also has benefit when coupled to this regular repeating surface architecture. While osseous tissues do not form in regular 3 dimensional structures it does follow a well-established pattern for growth which our device stimulates through the multiple surface preparation steps. The combination of stress induced remodeling of a stimulated bone cell in apposition to this prepared surface results in the overall device enhancing and accelerating the fusion of the device and bone structures. See image of bone structure and the Haversian Canals that typical form in the biologic structure noting the regular patterns at the cellular level e.g., Paul R. Odgren et al.; "Bone Structure" Encyclopedia of Endocrine Disease, Vol. 1, pp. 392-400 (2004) which is incorporated by reference herein.

Optimizing the pattern of the surface, but intentionally removing materials in patterns and through defined depths of features (e.g., teeth, grooves, sharp edges, ridges, anchoring fins (barbs) and shapes (e.g. U.S. Pat. No. 5,207,709, Picha also incorporated by referenced herein), may improve the biological growth of the tissues. Often this result is achieved with very large surface features machined or molded into implant devices. Larger features have an unintentional and difficult-to-measure side effect of localizing forces and can, over time, result in changing osseous integration. Therefore, the device becomes less stable or, through stress, induces necrosis remodeling. This is a commonly observed result in orthodontic treatment where loading is focused to move teeth in a patient's mouth to reposition dentition in a more effective location for mastication and esthetics. Although it is understood that loading can move and reshape bones, each patient and even each area of the skeletal structure is variable and therefore ideal large features often do not work in all applications and all patients. Other factors such as overall health, subsequent health conditions, degenerative conditions, and traumatic events add to this dynamic environment.

Other problems confront surgeons. For example, some surfaces are random and not well suited to the location of implantation, direction of loading, and forces acting on the implants due to daily activities. The results may include poor support of the spinal column or traumatic surgeries. These, in turn, may result in complications and increase patient traumatic suffering. Orientation of the surface patterns in parallel to the original surfaces is also enhanced by the depth of surface cuts and planes that can be designed to function more effectively in resisting directional loading and to be an advantage of a designed surface having three components, namely the width, length and also depth of the designed patterns.

To overcome the shortcomings of conventional spinal implants, a new spinal implant having an improved surface treatment is provided. An object of the present invention is to provide an implant surface having a pattern that is substantially uniform over the area of the implant that is intended to bond to the bone in which the implant is placed. A related object is to provide an improved surgically implantable device having on its surface a substantially uniform and bioactive micromorphology. It is another object of the invention to provide a process or processes for manufacturing such improved implant devices. A more specific object is to provide an improved process that yields a substantially uniform surface topography designed intentionally to enhance healing and long term function of surgically implantable devices.

It is to be understood that the present invention while directed primarily to spinal implants is not limited thereto. The advantageous implant surface created in practice of this invention obtains a surprising and unexpected osteointegration in the context of spinal repair that can be applicable in other situations. It is believed that the present invention can be applied in many medical circumstances where bone in-growth to the surface of a prosthetic device is important to the success of the cosmetic or therapeutic procedure. For example, lower body bone repair, e.g., foot/ankle, and dental prosthetic procedures utilizing prosthetic devices where bone in-growth is required are likely to have their success significantly improved by the use of devices having surfaces produced according to this invention.

SUMMARY OF THE INVENTION

The present invention provides an implantable device comprising a body, the body having a surface and a plurality of connections sized, in one embodiment, for placement into an intravertebral disc space. The surface has a defined, repeating, three-dimensional pattern that provides a surface area of bone-contacting features that allow for and encourage in-growth of bone and proteinaceous materials and biological attachment to a biocompatible material i.e., integration. The three dimensional surface morphology incorporates overlapping patterns of features in two dimensions as well as different and independent thereof dimensional depths for each of the features.

Another aspect of the invention is a method of making an implant device, the implant device comprising an implant body, the body defining a working surface, the surface having a first defined pattern on the surface; adding a second defined pattern on the surface, the second defined pattern overlapping the first defined pattern; and including at least one other defined pattern on the surface that overlaps with the first and second defined patterns.

It is to be understood that both the foregoing general description and the following detailed description are exemplary, but are not restrictive, of the invention.

BRIEF DESCRIPTION OF THE DRAWINGS

The invention is best understood from the following detailed description when read in connection with the accompanying drawings and the attached claims. It is emphasized that, according to common practice, the various features of the drawings are not to scale. On the contrary, the dimensions of the various features are arbitrarily expanded or reduced for clarity. Included in the drawings are the following figures:

FIGS. 6A, 6B, 6C, 6D, 6E, and 6F show SEM images of PEEK (A, B), sTiAIV (C, D), and rTiAIV (E, F) surfaces at low and high magnifications.

FIGS. 7A-7D show relative size limitations and surface roughness features of this invention.

In FIG. 8 the depth is greatest for 1 and ascends till step 3 with the sizes of the cuts increasing from 1 to 3.

DETAILED DESCRIPTION OF THE INVENTION

Figure 1A:
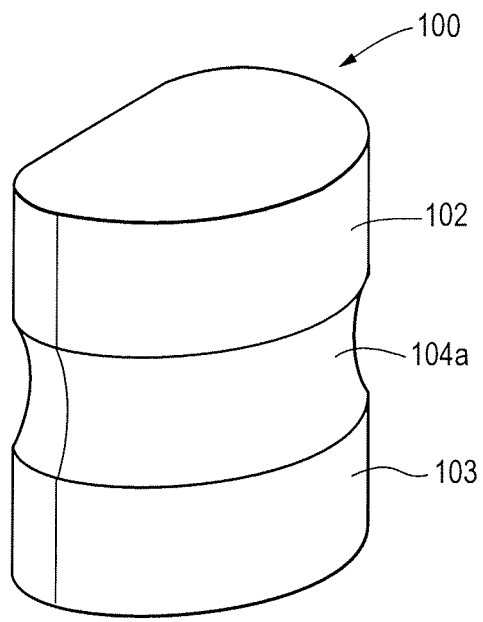
FIG. 1A shows a perspective view of a healthy vertebral column including a disc separating vertebrae.
Figure 1B:
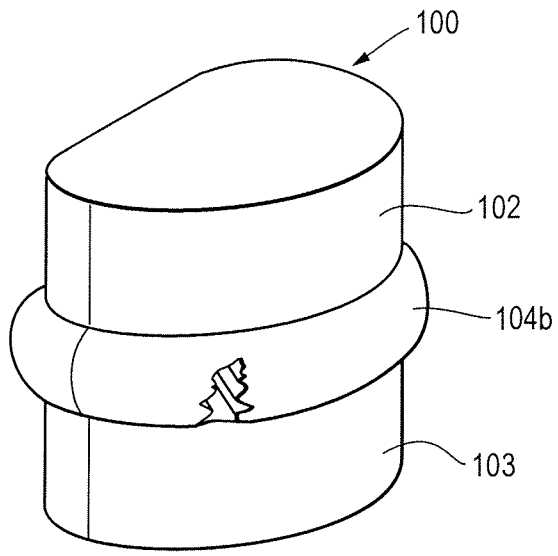
FIG. 1B shows a perspective view of a vertebral column including a damaged disc and vertebrae.

Referring now to the drawings, in which like reference numbers refer to like elements throughout the various figures that comprise the drawings, FIG. 1A shows a spinal column 100 including an upper vertebra 102 and a lower vertebra 103 separated by a healthy, flexible disc 104a. FIG. 1B shows the spinal column 100 with the upper vertebra 102 and the lower vertebra 103 separated by a damaged or collapsed disc 104b. The damaged disc 104b typically requires surgical intervention to attain fusion and stabilization for complete healing and the relief of pain. A device according to this invention, e.g., a spinal implant, is used to replace the damaged disc 104b and provides strong initial stability, rapid healing, and bone repair.

Figure 2:
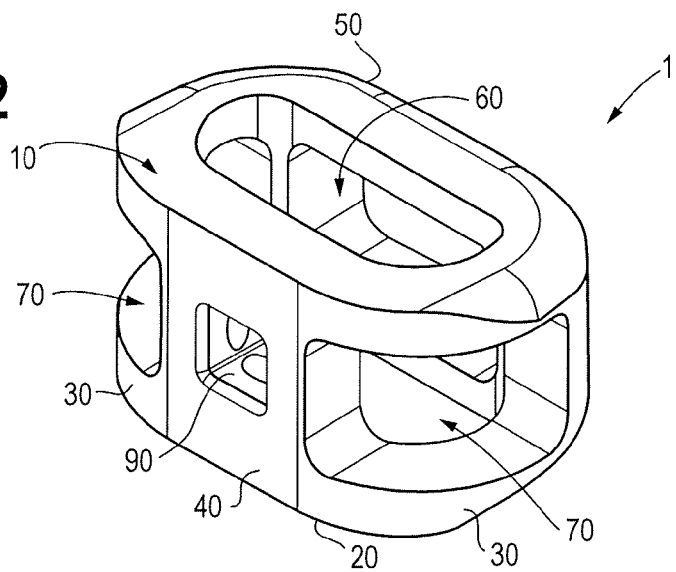
FIG. 2 shows a perspective view of a prior art spinal implant.

As illustrated in FIG. 2, certain embodiments of the present invention include an interbody spinal implant 1 that serves as a spacer between adjacent vertebrae. The implant 1 may be comprised of titanium, a titanium alloy, organic polymers such as polyaryletheretherketone ("PEEK") materials, ceramics, and other suitable materials known to people of skill in the art. The implant 1 comprises an implant body 5 with a top surface 10, a bottom surface 20, opposing lateral sides 30, and opposing anterior 40 and posterior 50 portions. The implant 1 has a sharp edge 8 where the anterior portion 40 meets the top surface 10 and where the anterior portion 40 meets the bottom surface 20. A delivery device (not shown) can engage opening 90 in the anterior portion 40 of the implant 1, allowing the user to manipulate the implant 1 during placement between vertebrae.

The implant 1 is substantially hollow and has a generally oval-shaped transverse cross-sectional area with smooth and/or rounded lateral sides and rounded posterior-lateral corners. The implant 1 includes at least one aperture 60 that extends the entire height of the implant body. The implant 1 may further include at least one aperture 70 that extends the entire transverse length of the implant body. These transverse apertures 70 may provide improved visibility of the implant 1 during surgical procedures to ensure proper implant seating and placement, and may also improve post-operative assessment of implant fusion. Still further, the substantially hollow area may be filled with cancellous autograft bone, allograft bone, demineralized bone matrix (DBM), porous synthetic bone graft substitute, bone morphogenic protein (BMP), or combinations thereof, to facilitate the formation of a solid fusion column within the patient's spine.

Figure 3A:
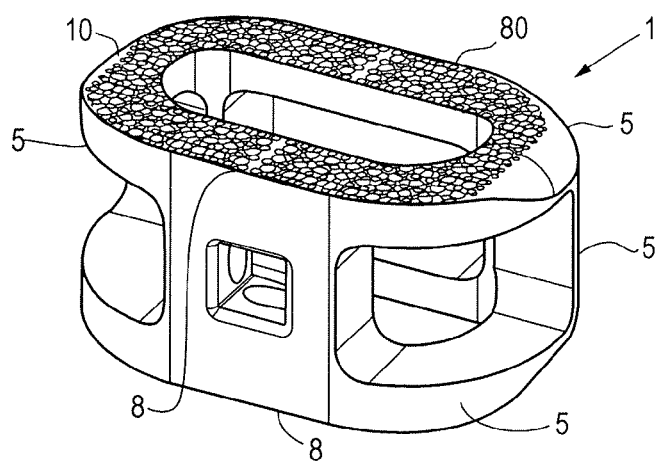
FIG. 3A shows a perspective view of the spinal implant of the present invention.
Figure 3B:
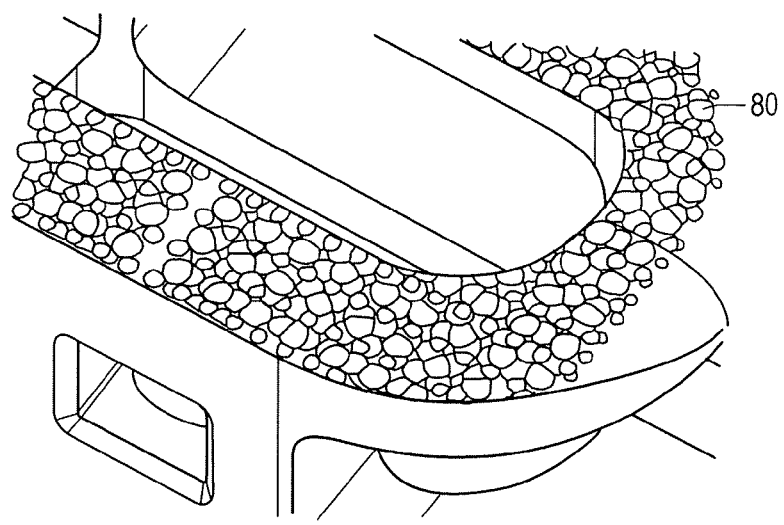
FIG. 3B shows a partial perspective view highlighting a portion of the implant illustrated in FIG. 3A.

As illustrated in FIGS. 3A and 3B, the implant 1 further includes a designed surface topography 80. The designed surface topography 80 is provided on at least a portion of the top surface 10, the bottom surface 20, or both the top and bottom surfaces 10, 20 of the implant 1 for gripping adjacent bone and inhibiting migration of the implant. Preferably, each surface 10 and 20 has a designed surface topography 80 that promotes anchoring and healing of spinal tissues.

It is generally believed that the three-dimensional surface of the implant 1 determines its ultimate ability to integrate into the surrounding living bone. Without being limited by theory, it is hypothesized that the cumulative effects of at least implant composition, implant surface energy, and implant surface topography play a major role in the biological response to, and osteointegration of, the implant 1.

The addition of macro, micron/submicron and nano sized features in the ranges as stated in the table below stimulate the growth of the bone cellular structures by working in concert with well understood bone modeling and structures. The overall 3 dimensional shape of bone is not of a repeating structure but at a cellular level as in the Haversian Canal the structure is repeating and regular. By stimulating the biological behavior of the bone cells the resulting stimulation works in concert with the other structural features of the invention and balances the performance of the implant as a fusion device with sufficient resistance to expulsion and mobility to succeed in the initial stabilization of the device and the long term incorporation of rigid fusion of the vertebrae.

(Ra) are applied on top of the three machined or etched expulsion features and cover the entirety of the implant and are also on the surfaces of the implant in areas where there is not an anti-expulsion surface pattern. The nano sized features unlike many other published structures are indented into the surface or subtracted from the base material through post processing etching and blasting methods and therefore have an inherent structural rigidity that is not found in protruding tube features in the nano size range.

"Osteointegration" as that term is used here is intended to mean the formation of a direct structural and functional interface between an artificial implant, and living boned. In a narrower sense, osteointegration occurs without the presence of soft tissue between bone and implant.

Thus, implant fixation may be, at least in part, dependent on the attachment and proliferation of osteoblasts, and like functioning, cells upon the implant surface. Still further, it appears that these cells attach more readily to relatively rough surfaces rather than smooth surfaces. In this manner, a surface may be bioactive due to its ability to facilitate cellular attachment and osteointegration. Without being limited by theory, it is believed that the designed surface topography and predefined depths of these features 80 may better promote the osteointegration of the implant 1. The designed surface topography 80 may also better grip the vertebral endplate surface(s) and inhibit implant migration upon placement and seating. This is accomplished through the designed patterns of the features including the depths of the overlapping patterns.

Thus, the present invention provides the implant 1 having an implant body 5 that defines a designed surface topography 80 that is both three dimensional and intentionally patterned. The designed surface topography 80 is produced in multiple steps using tooling of a specified shape and size. The designed surface topography 80 is adapted to create a large surface area of bone-contacting features that allow for in-growth and biological attachment to a biocompatible material.

The designed surface topography 80 of an implant 1 of this invention has specific patterns. By overlapping these patterns, the designed surface topography 80 may be used as an integration surface with features of a desirable size for bone growth (specifically implant in-growth) and attachment and to aid in resisting forces that act on the implant 1, thereby improving stability and overall success of the procedure. The designed surface topography 80 with a defined pattern of the implant 1 facilitates the installation of the implant 1 and enhances the initial, intermediate, and long-term stability of the implant 1.

The designed surface topography 80 is created using predictable and repeatable process steps, such as mechanical or chemical machining, photo etching or adaptations of laser or plasma welding technologies. These steps allow for variations of the surface patterns on individual implant working surface so that areas that may benefit from more or less aggressive features may be formed. The three dimensional patterns can also be varied is ways that can be used to fine tune

| Surface Feature Size and Roughness | | | | | |
|---|---|---|---|---|---|
| Macro Size (Rz) | Roughness (Ra) | Micron/Submicron Size (Rz) | Roughness (Ra) | Nano Size (Rz) | Roughness (Ra) |
| 50 µm-200 µm | 10 µm-30 µm | 500 µm-20 µm | 5 µm-10 µm | 200 nm-500 nm | .5 µm-5 µm |

These features in the ranges of peak size or crest to crest of the indentation (Rz) and with an average surface roughness various areas of the implant bodies initial fixation due to contact with the vertebral body and it's relative construction.

More specifically, the use of microscopic mechanical or chemical machining, photo etching or adaptations of laser or plasma welding technologies generating repeating patterns in multiple overlapping steps onto a surface that is refined with e.g., a post machining and abrasive media blasting step, or acid etching, results in a macro and micro designed surface topography 80 that effectively integrates with bone. In addition, the designed surface topography 80 may be oriented to resist biological loading better than randomly generated surfaces.

By analogy, treads on automobile tires are designed with specific functions in mind: grip in the forward direction, for example, and stability in the lateral direction. Similarly, the designed selected, planned or strategically chosen surface topography 80 of the present invention can be predetermined with specific functions in mind. (By "predetermined" is meant determined beforehand, so that the predetermined pattern is determined, i.e., chosen, selected or at least known or in mind, before processing begins and in view of the post-implant medical environment). The designed surface topography 80 on the top surface 10 in the anterior portion 40 may have larger and sharper features to resist expulsion of the implant 1 from between the vertebrae, for example, while the designed surface topography 80 on the top surface 10 in the posterior portion 50 may have smaller and less sharp features to facilitate placement of the implant 1. This flexibility gives the designer options to achieve desired performance characteristics and the designer can both optimize and enhance the performance of the implant 1 having the designed surface topography 80. Preferably, the implant 1 does not have any unintentional sharp edges or protrusions (excepting sharp edges 8 which are intentionally provided to permit implant 1 to resist expulsion from between adjacent vertebra). These sharp edges or protrusions sometimes result in focal points for loading and the resulting loss of osseous tissues through stress-induced bone loss. This is also considered in concert with the structural properties of the vertebral body, which is commonly stiffer on the outer edges and has greater mobility towards their center surfaces. The implant surface that has synthetic and or biologically derived materials applied to it allows for "seeding" in specific locations of these materials acting in concert with the microscopic surface enhancements generated in the production process. With or without the addition of growth-enhancing materials and surface geometry, the designed surface topography 80 has features in a defined size range that are beneficial to the biological growth and remodeling of bone tissues subjected to loading in several directions.

The designed surface topography 80 of the implant 1 is the connection point for the load-bearing or working surface of the implant 1 and the live osseous tissue of the vertebrae. The designed surface topography 80 allows for initial stabilization and long-term bone in-growth and fusion. Larger surface areas and a smooth and contoured surface provide more assured and effective initial, intermediate, and long-term outcomes and overall benefit to a patient.

Using micro surfaces created through subtractive chemical or mechanical processes is an achievable and commercially viable way to increase the surface area for dissipating variable loads and compensating for variable bone conditions. Smaller features that allow for dissipated forces but having a regulated, designed pattern are beneficial in treating the largest possible number of patients having the largest number of variables.

Through careful design of readily available micro machine tools, photo etching, and other processes of microscopic machining and advanced manufacturing equipment and adaptation of these processes using repeating and multiple overlapping patterns of varying depths, surfaces that have the same roughened contours as chemically etched surfaces may be achieved. The patterns, depth diameters, and other manufacturing process settings generate a designed surface topography 80 having three-dimensional contour, directional stability, and long-term success. The addition of general acid or abrasive media post machining preparation provides the benefits of refining the surface, removing sharp edges resulting from the machining, and adding a micro texture to the implant integration surface.

Exemplary embodiments of the implant body comprise many various bodies of various sizes and biocompatible materials that have surface enhancements consistent with the designed surface topography 80 of machined and acid etching refined surfaces. The designed surface topography 80 can be formed in multiple steps using very small tooling often referred to as micro drills or milling cutters in high speed, highly precise, milling equipment. These practices are contrary to common efforts to remove large amounts of material as quickly as possible. Optimization of the surface geometry and the ability to define repeating patterns to predefined depths is beneficial to the overall product design can be achieved using these processes and others.

The following exemplary process steps are included to more clearly demonstrate the overall nature of the invention. These steps are exemplary, not restrictive, of the invention. The sequential process steps shown in FIGS. 4A, 4B, and 4C illustrate multiple layers and steps of implant machining.

Figure 4A:
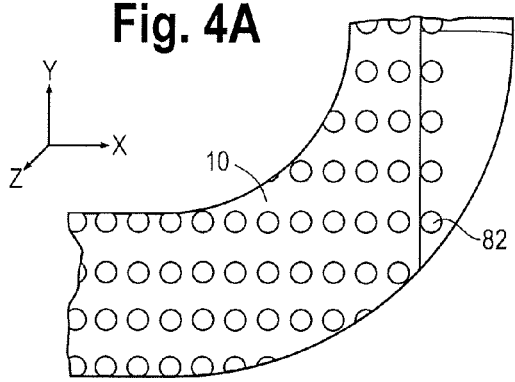
FIG. 4A shows a partial top view of a surface of the implant of the present invention following a first exemplary processing step.
Figure 4B:
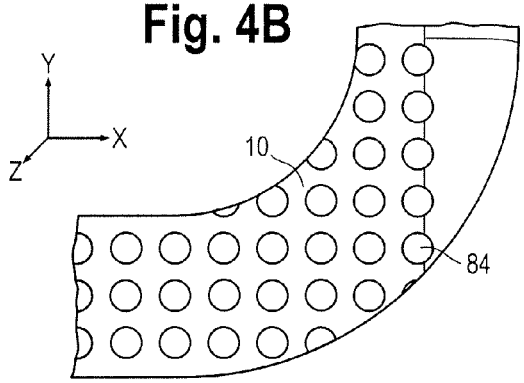
FIG. 4B shows a partial top view of the surface of the implant of the present invention shown in FIG. 4A, following a second exemplary processing step.

As shown in FIG. 4A, the first process step creates a first feature 82 of the designed surface topography 80 on the top surface 10 of the implant 1. The first feature 82 is typically the deepest feature of the designed surface topography 80 and may be, for example, 0.021 inches deep (or more) into the surface of the implant 1 (along the Z axis as illustrated). A wide variety of processes can be applied to create the first feature 82. As illustrated, the first feature is a spherical indent which might be created, for example, by the use of a ball-shaped tool (e.g., by "peening" or drilling). In processing circumstances where surface material is displaced to create surface topography it will be understood that subsequent processing or finishing steps e.g., polishing, may be employed to remove incidentally-created surface artifacts which are not part of the feature.

The designed surface topography 80 of the implant 1 is produced by overlapping several features. In FIG. 4B, the second process step creates a second feature 84 of the designed surface topography 80 of the implant 1 but up to the depth of the first feature. The second feature 84 is typically the second deepest feature of the designed surface topography 80 and may be, for example, 0.014 inches deep into the surface of the implant 1. A wide variety of processes can be applied to create the second feature 84. The depth and X-Y placement of the second feature 84 are selected so that the second feature 84 does not directly overlap and wipe out the first feature 82 (to highlight the second feature 84 and for purposes of clarity the first feature 82 is not shown in FIG. 4B although the first feature 82 exists in combination with the second feature 84). The depth variations and alignment to the expected load direction will have the same net effect as a single feature of the same depth, but in other lower loaded directions will minimize focused loading and reduce stresses that the bone is subjected to when lower loading is applied. As with the first feature 82 incidentally-created process artifacts e.g., burrs, splays, may need to be removed using well known techniques.

Figure 4C:
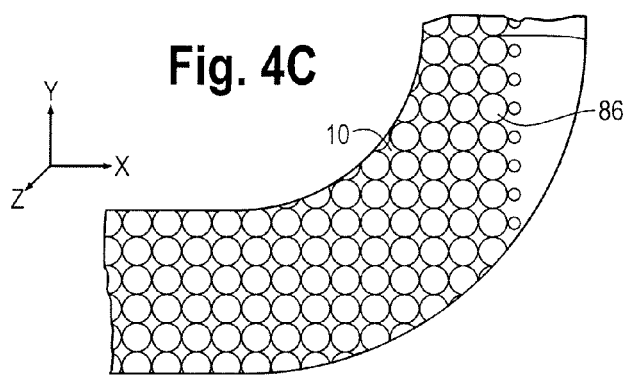
FIG. 4C shows a partial top view of the surface of the implant of the present invention shown in FIG. 4B, following a third exemplary processing step.

As shown in FIG. 4C, the third process step creates a third feature 86 of the designed surface topography 80 of the implant 1. The third feature 86 is typically the shallowest feature of the designed surface topography 80 and may be, for example, 0.007 inches deep into the surface of implant 1 but less than the depth of the second feature 84. A wide variety of processes can be applied to create the third feature 86. The depth and X-Y placement of the third feature 86 are selected so that the third feature 86 does not directly overlap and wipe out the first feature 82 or the second feature 84 (to highlight the third feature 86 and for purposes of clarity the first feature 82 and the second feature 84 are not shown in FIG. 4C although the first feature 82 and the second feature 84 exist in combination with the third feature 86). Note that the rightmost column of the third feature 86 as illustrated in FIG. 4C appears smaller than the remainder of the third feature 86 only because the third feature 86 extends beyond the top surface 10 and onto the lateral side 30 a short distance.

Figure 4D:
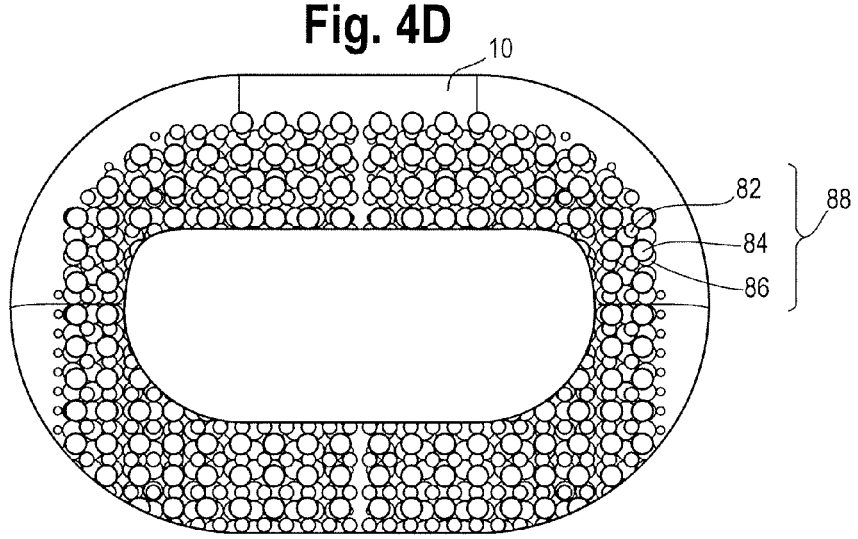
FIG. 4D shows a top view of the completed surface of the implant of the present invention following the processing steps shown in FIGS. 4A, 4B, and 4C.

Of course, processes with more or fewer than three steps can be used to create any predetermined pattern for the designed surface topography 80. And each process step can create a feature that differs (in type, size, shape, location, and other characteristics) from the features illustrated in FIGS. 4A, 4B, and 4C. FIGS. 4A, 4B, and 4C depict exemplary process steps with different surfaces. As completed for the example illustrated, the designed surface topography 80 following the multi-step sequential application of process steps (shown as bracket 88 and indicating the completed workpiece or working surface) and final working surface of implant body 5 is shown in FIG. 4D. The implant 1 illustrated in FIG. 4D combines machined and acid etched micro surfaces that behave in a similar manner with regard to the bone tissues, but add directional stability by having an organized pattern that resists loading and potential movement of the implant 1.

The designed surface topography 80 of the implant 1 is produced by overlapping several features. This results in a large surface area of defined geometric shapes and patterns. Preferably, the process steps include repeating shapes between the machining steps to produce a large surface area having a defined pattern. The designed surface topography 80 may also be refined using mechanical, focused energy or chemical processes to improve the implant surface.

Thus, the designed surface topography 80 may be obtained through a variety of techniques including, without limitation, chemical or acid etching, shot peening, plasma etching, laser etching, or abrasive blasting, such as sand or grit blasting. In one process step embodiment of the present invention, a roughened surface topography is obtained via the repetitive masking and chemical or electrochemical milling processes described in U.S. Pat. Nos. 5,258,098; 5,507,815; 5,922,029; and 6,193,762, each incorporated herein by reference. By way of example, an etchant mixture of nitric acid and hydrofluoric acid (HF) may be repeatedly applied to a titanium surface to produce an average etch depth of about 0.021 inches. Interbody spinal implants 1 may be comprised, in accordance with preferred embodiments of the present invention, of titanium or a titanium alloy having an average surface roughness of about 100 µm on the top surface 10 and on the bottom surface 20. Surface roughness may be measured using a laser profilometer or other standard instrumentation.

The implant surface is produced using defined and adapted tooling that, when patterns of these features are overlapped in a predetermined manner, result in an improved surface capable of sustaining osseous in-growth under loading. Various chemicals, such as acids, may be used to refine the contours of the implant surface. The result of such refinement is a relatively smooth surface free from manufacturing debris and well adapted to biological behavior of bone tissues.

Due to their small size and limited operational access, implants 1 of the exemplary type are typically difficult to manipulate and precisely place without instruments. The body of the implant typically includes at least three, and sometimes more than three, instrument connections (such as the opening 90) that can be threaded, force fit, or snap fit together to rigidly connect the implant 1 and withstand placement in the vertebrae. The force fit of the implant 1 into the intravertebral space creates initial stability of the device and incorporates the bone tissues into the surface of the implant 1.

EXAMPLES

Background

Titanium implants with physical-chemical modifications such as micron or submicron scale topographic features have been shown to increase osteoblast differentiation and local factor production in vivo and to increase pen-implant bone formation and decrease healing time in vivo. Polyetheretherketone (PEEK) is used as a cage or spacer in vertebral interbody fusion to maintain spinal alignment and segmental stability while facilitating bony fusion. The aim of this analysis was to elucidate whether common intervertebral materials such as PEEK and titanium alloy (Ti6Al4V) induce osteoblast maturation and generate an osteogenic environment.

Methods

The methods employed herein are shown below.

Figure 9:
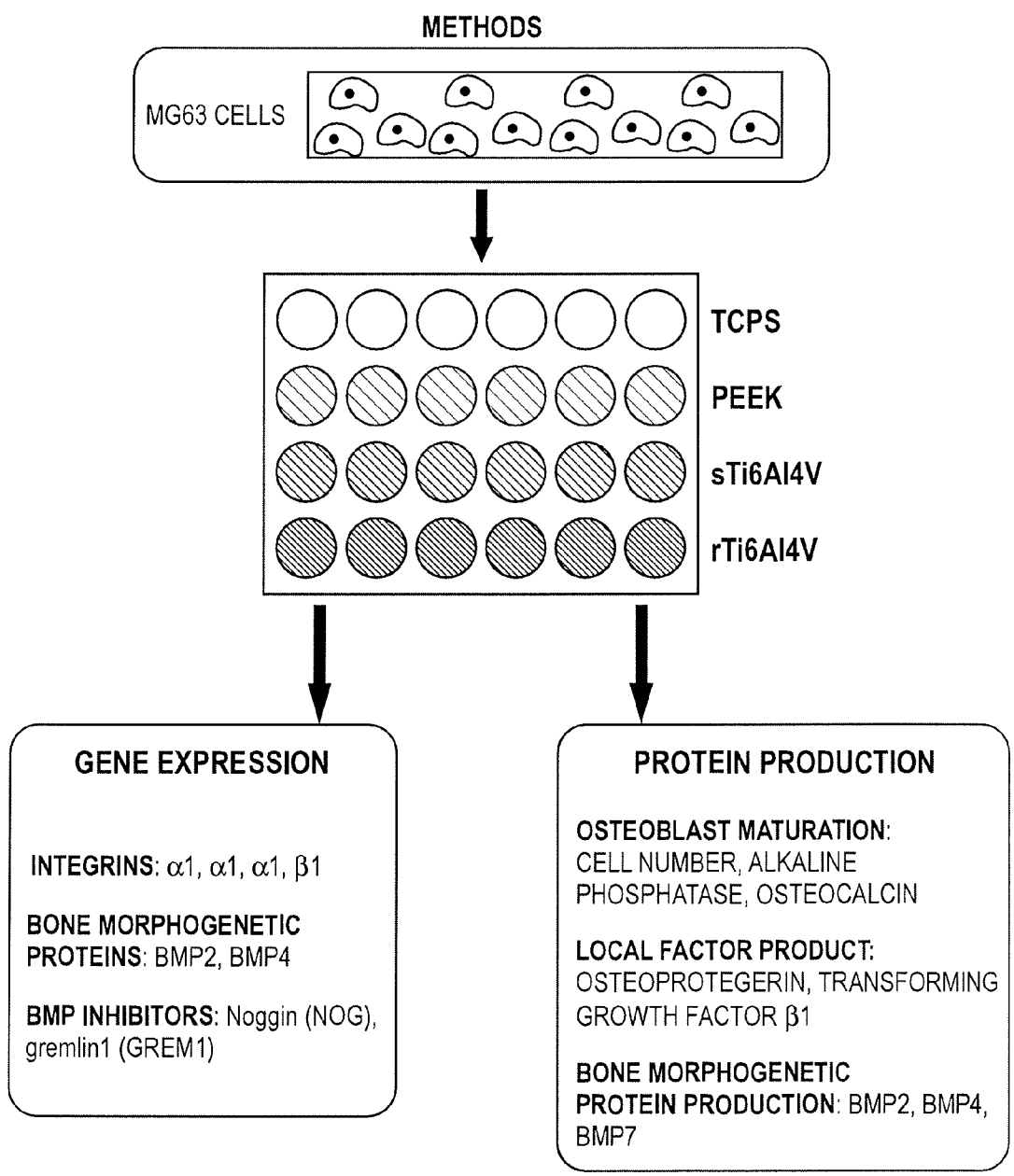
FIG. 9 is a schematic representation of human osteoblast-like MG63 cell cultures in accordance with an embodiment of the present invention.
Figure 10B:
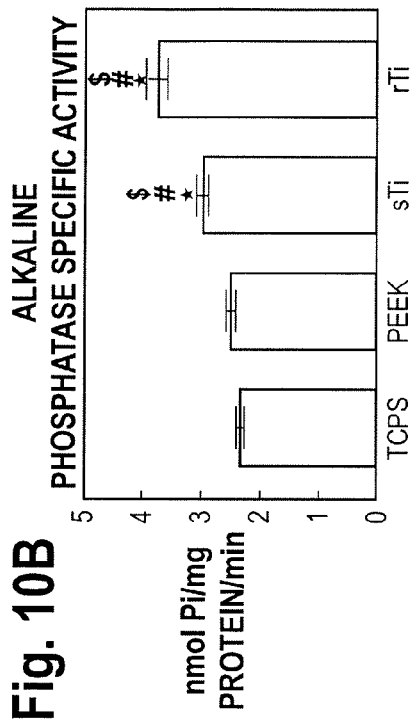
FIGS. 10A, 10B, 10C, and 10D are tables showing values obtained from human MG63 osteoblast-like cells harvested 24 hours after confluence on TCPS.
Figure 10D:
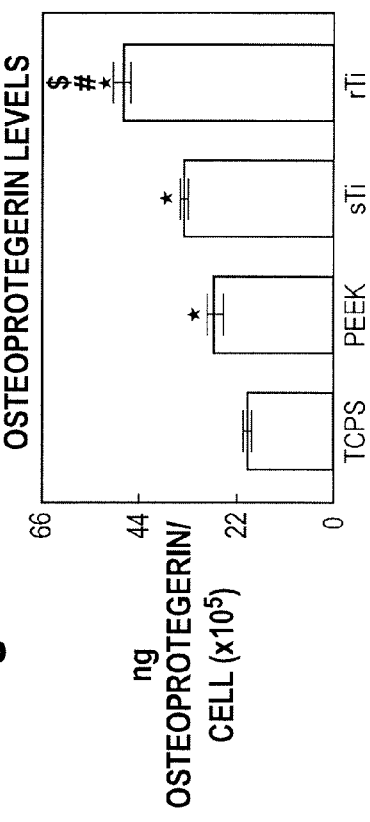
Figure 10A:
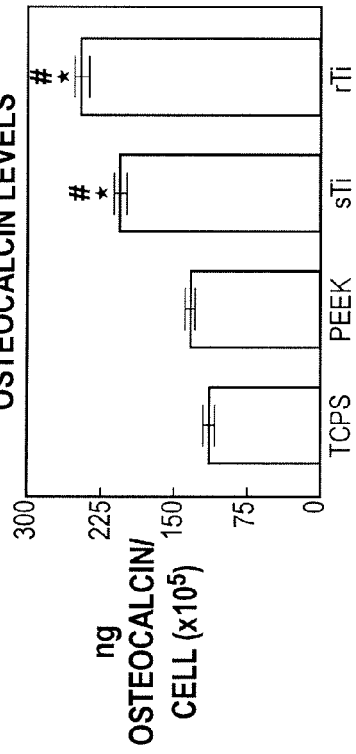
Figure 10C:
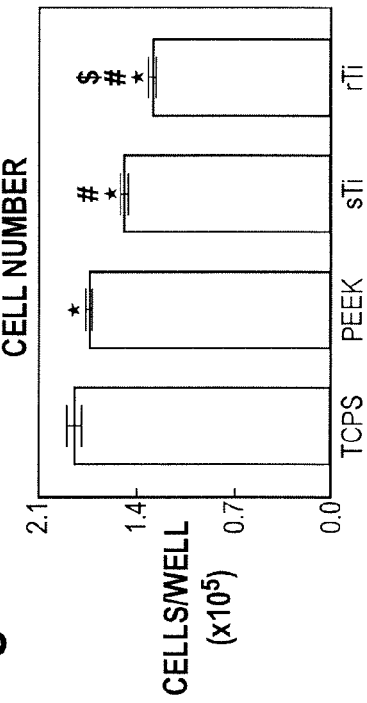
Figure 11A:
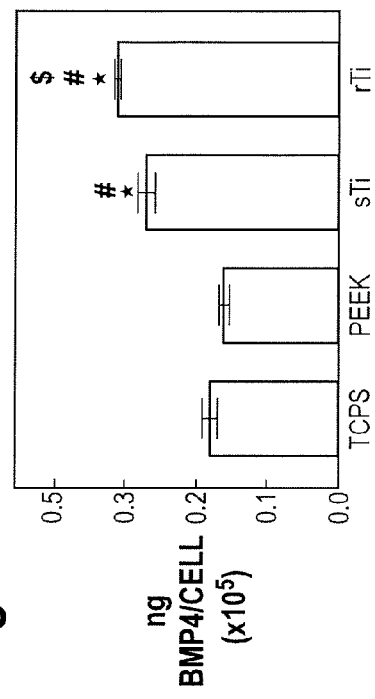
FIGS. 11A, 11B, 11C, and 11D are tables showing values obtained from human MG63 osteoblast-like cells harvested 24 hours after confluence on TCPS.
Figure 11B:
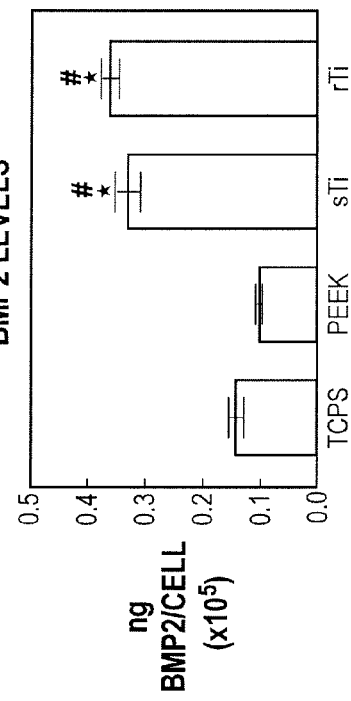
Figure 11C:
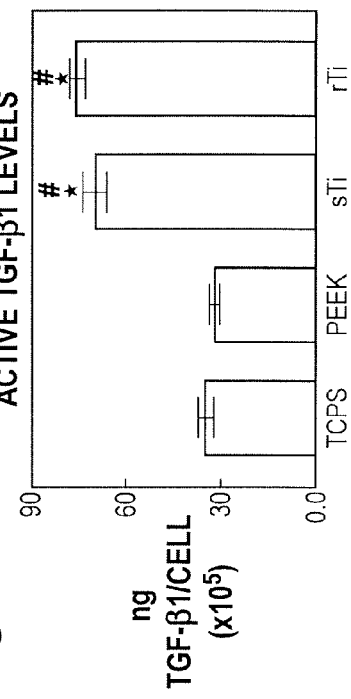
Figure 11D:
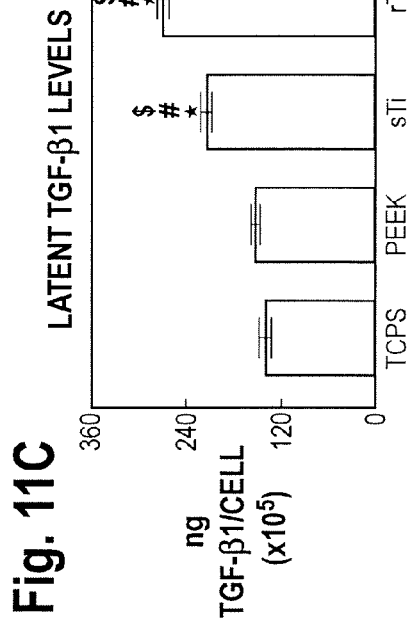
Figure 12A:
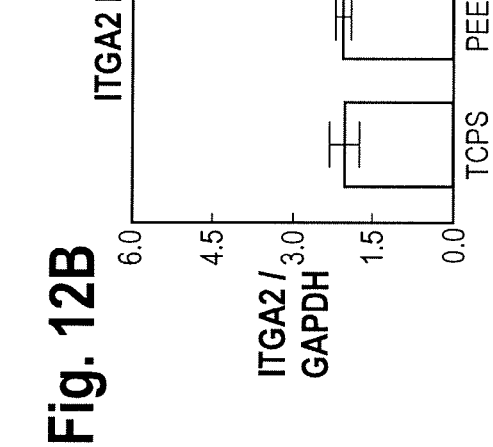
FIGS. 12A, 12B, 12C, 12D, 12E, 12F, 12G, and 12H are tables showing results from human MG63 osteoblast-like cells harvested 12 hours after confluence on TCPS.
Figure 12B:
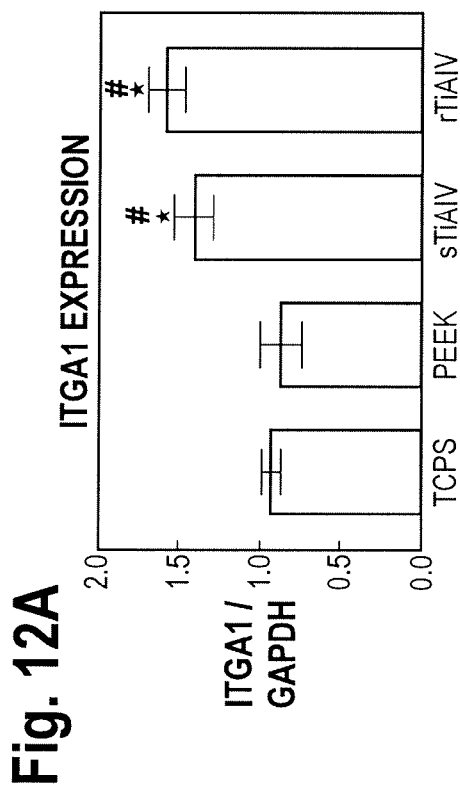
Figure 12C:
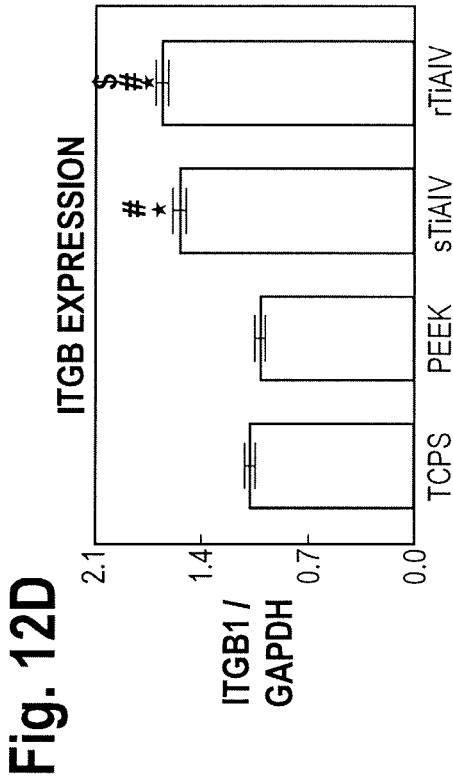
Figure 12D:
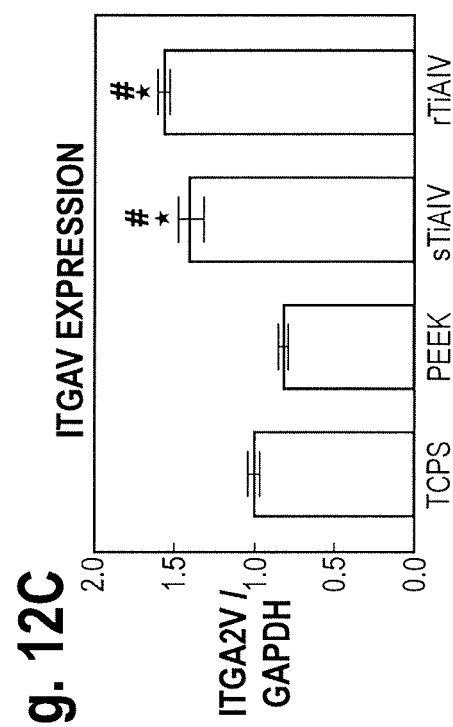
Figure 12E:
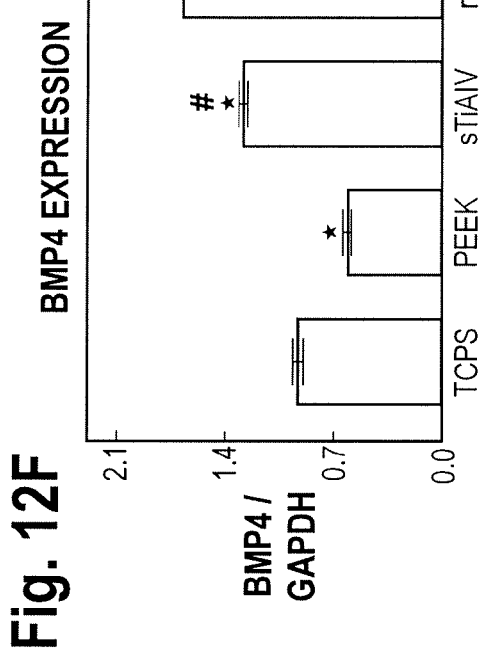
Figure 12F:
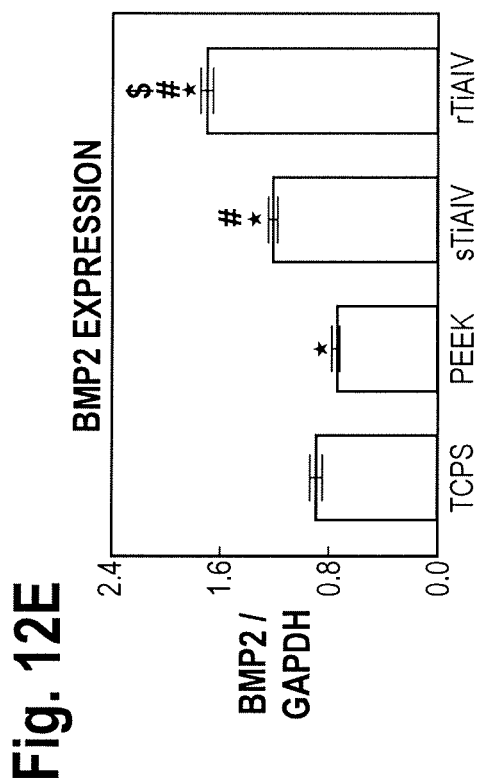
Figure 12G:
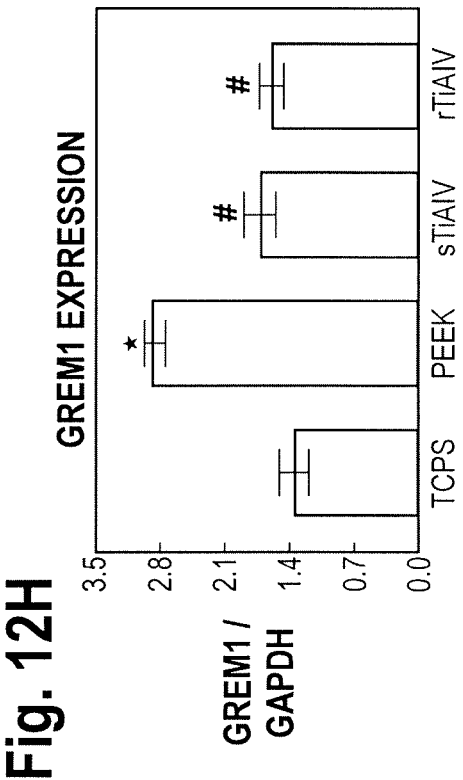
Figure 12H:
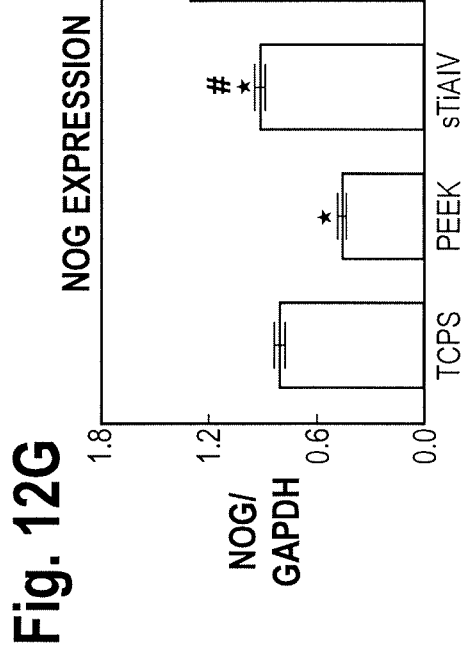

Human osteoblast-like MG63 cells were cultured on tissue culture polystyrene (TCPS), PEEK, or smooth [sTi6Al4V, $S_a>90$ nm] and rough [rTi6Al4V, $S_a=1.81$ µm] Ti6Al4V surfaces as shown in FIG. 9. Gene expression was measured by qPCR. Osteoblast maturation was assessed by analysis of cell number, alkaline phosphatase activity (ALP), and secreted osteocalcin, osteoprotegerin, TGF-B1, BMP2, BMP4, and BMP7. Data are mean±SEM (n=6/condition), analyzed by ANOVA with Bonferroni's modification of Student's t-test.

Results

Figure 5A:
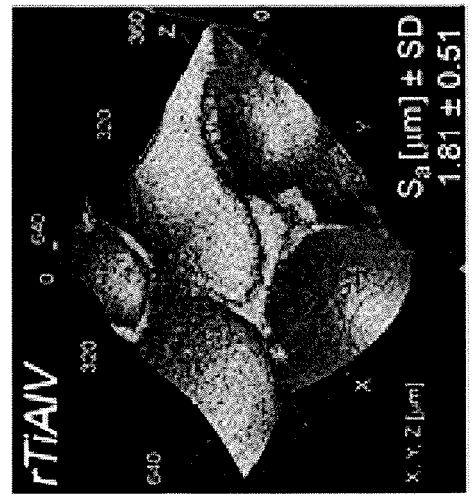
FIGS. 5A, 5B, and 5C show confocal laser microscopy images and average-roughness ($S_a$) values of PEEK (A), sTi-AIV (B), and rTiAIV (C) surfaces of 644×644 μm² field.
Figure 5B:
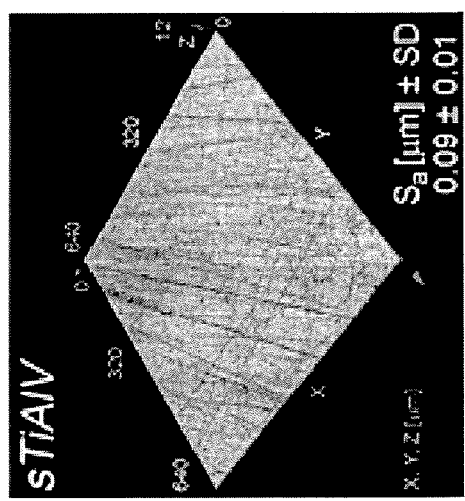
Figure 5C:
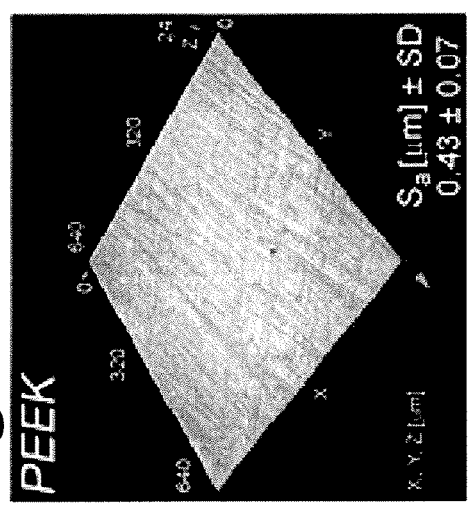
Figure 7A:
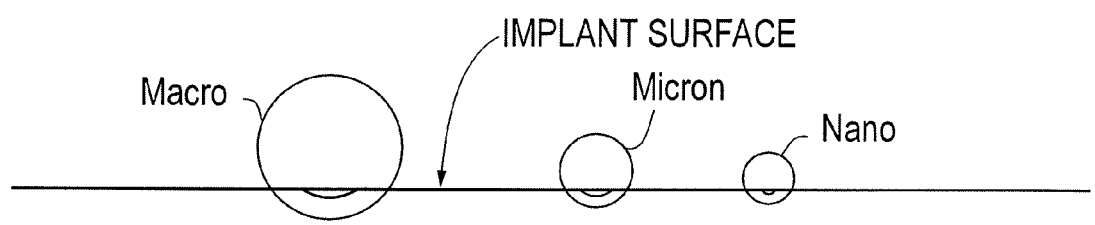
FIG. 7A Shows the three features; Macro, Micron/Submicron and Nano size.
Figure 7B:
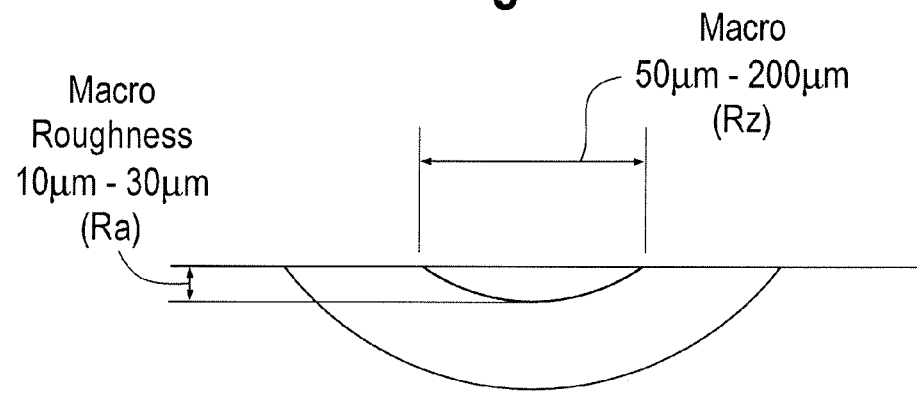
FIG. 7B Shows the size range and roughness of the Macro feature.
Figure 7C:
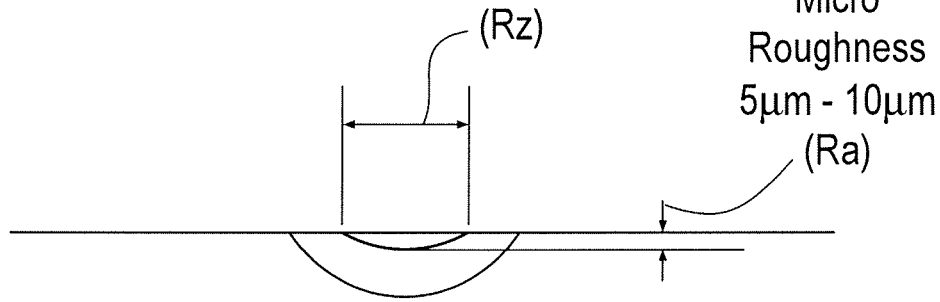
FIG. 7C Shows the size range and roughness of the Micron/Submicron features.
Figure 7D:
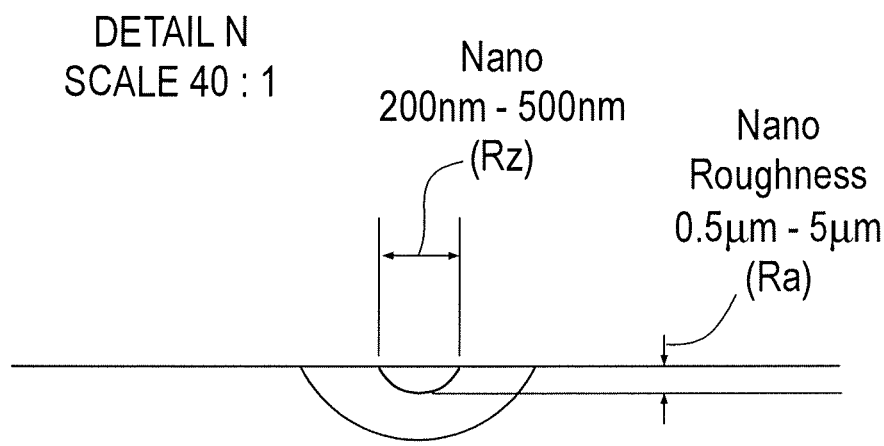
FIG. 7D Shows the size range and roughness of the Nano feature.
Figure 8:
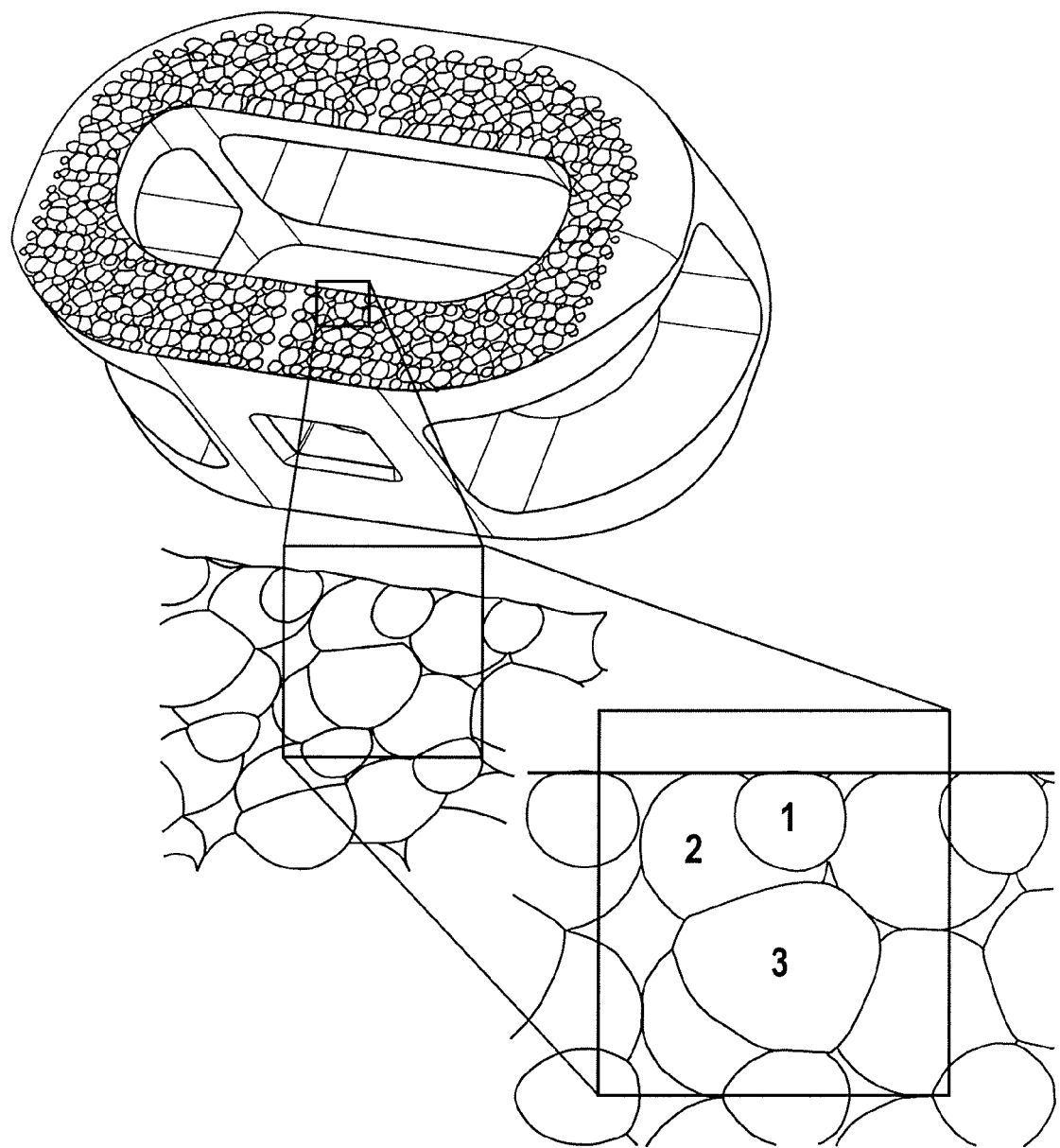
FIG. 8 shows an exemplary dimple pattern surface of this invention in macroscopic and microscopic detail. The patterns of dimples 1, 2, 3 are overlapping, but they are sized and aligned so as not to either remove the previous dimple.

FIGS. 5A, 5B, and 5C. Confocal laser microscopy images and average-roughness ($S_a$) values of PEEK (A), sTiAIV (B), and rTiAIV (C) surfaces of 644×644 µm² field.

FIGS. 6A, 6B, 6C, 6D, 6E, and 6F. SEM images of PEEK (A, B), sTiAIV (C, D), and rTiAIV (E, F) surfaces at low and high magnifications.

Human MG63 osteoblast-like cells were harvested 24 hours after confluence on TCPS.

Cell number, alkaline phosphatase specific activity in cell lysates and levels of osteocalcin, osteoprotegerin, active TGF-β1, latent TGF-β1, BMP2 and BMP4 in the conditioned media were measured. *$p<0.05$, v. TCPS; #$p<0.05$, v. PEEK; $$p<0.05$, v. sTiAIV. The values obtained are shown in FIGS. 10A-D and FIGS. 11-A-D.

Human MG63 osteoblast-like cells were harvested 12 hours after confluence on TCPS. Levels of mRNA for integrins alpha 1 (ITGA1), alpha 2 (ITGA2), alpha v (ITGAV), and beta 1 (ITGB1), BMP2 (A) and BMP4, and BMP inhibitors noggin (NOG) and gremlin 1 (GREM1) were measured by real-time qPCR and normalized to GAPDH. *$p<0.05$, v. TCPS; #$p<0.05$, v. PEEK; $$p<0.05$, v. sTiAIV. Results are shown in FIGS. 12A-H.

Discussion

The results indicate that osteoblasts on Ti6Al4V surfaces present a more mature phenotype than osteoblasts grown on PEEK. Cells on Ti6Al4V, but not PEEK, produce an osteogenic environment. Osteoblasts cultured on Ti6AI4V produce and regulate BMP pathway molecules, increasing BMP2, BMP4, BMP7, and physiologic BMP inhibitors. One reason for the differential response of osteoblasts to PEEK and TiALV may result from differences in integrin expression downstream signaling by these receptors. Taken together, surface properties, including the composition of the bulk material, are important in directing cell response to implant materials, ultimately affecting implant success. The results demonstrate that Ti6AI4V surfaces positively modulate osteoblast maturation and regulate BMP signaling.

The instrumentation and installation practices of this invention are used in not only spinal surgery, but also in common orthopedic treatment of many of the bones and joints in the body. Common hip and knee implants often use a force fit or interference fit to initially stabilize the implants and promote long-term success. These instruments and the connection to the implants are correspondingly durable and robust enough to withstand loading, impacts, and forces resulting from the procedures.

Although illustrated and described above with reference to certain specific embodiments and examples, the present invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges.

The invention claimed is:

1. An implantable device, comprising
a body having a top surface and a bottom surface, the top surface, the bottom surface, or both the top and bottom surfaces having a surface topography comprising first, second, and third surface patterns without sharp protrusions;
the first surface pattern including a plurality of dimples having a first depth dimension, the second surface pattern including a plurality of dimples having a second depth dimension, and the third surface pattern including a plurality of dimples having a third depth dimension, the first depth dimension being greater than the second depth dimension, and the second depth dimension being greater than the third depth dimension, wherein a portion of the second surface pattern overlaps the first surface pattern and a portion of the second surface pattern does not overlap the first surface pattern, and a portion of the third surface pattern overlaps the second surface pattern and a portion of the third surface pattern does not overlap the second surface pattern, and wherein the third surface pattern supports in-growth of bone into the body and positively modulates osteoblast maturation and regulates bone morphogenic protein signaling.

2. The implantable device of claim 1, wherein the surface topography is oriented to have higher load resistance to a specific load direction.

3. The implantable device of claim 1, wherein the plurality of dimples of the first surface pattern and of the second surface pattern comprises semi-spheres.

4. The implantable device of claim 1, wherein the first surface pattern comprises macro sized features and the second surface pattern comprises micro sized features.

5. The implantable device of claim 1, wherein the first surface pattern comprises macro sized features, the second surface pattern comprises micro sized features, and the third surface pattern comprises nano sized features.

6. The implantable device of claim 5, wherein the macro sized features have a macro size Rz of 50 µm to 200 µm and a roughness Ra of 10 µm to 30 µm, the micro sized features have a micro size Rz of 500 nm to 20 µm and a roughness Ra of 5 µm to 10 µm, and the nano sized features have a nano size Rz of 200 nm to 500 nm and a roughness Ra of 0.5 µm to 5 µm.

7. The implantable device of claim 1, wherein the body comprises titanium or an alloy thereof.

8. The implantable device of claim 1, wherein the surface topography is substantially uniform across the top surface, the bottom surface, or both the top and bottom surfaces.

9. The implantable device of claim 1, wherein the first and second surface patterns stabilize the body when the top surface, bottom surface, or both the top and bottom surfaces contact bone.

10. An implantable device, comprising
a body having a top surface and a bottom surface, the top surface, the bottom surface, or both the top and bottom surfaces having a surface topography comprising first, second, and third surface patterns without sharp protrusions;
the first surface pattern including a plurality of dimples having a first depth dimension, the second surface pattern including a plurality of dimples having a second depth dimension, and the third surface pattern including a plurality of dimples having a third depth dimension, the first depth dimension being greater than the second depth dimension, and the second depth dimension being greater than the third depth dimension, wherein a portion of the first surface pattern partially overlaps the second surface pattern and a portion of the third surface pattern partially overlaps the second surface pattern, and wherein the third surface pattern supports in-growth of bone into the body and positively modulates osteoblast maturation and regulates bone morphogenic protein signaling.

11. The implantable device of claim 10, wherein the surface topography is oriented to have higher load resistance to a specific load direction.

12. The implantable device of claim 10, wherein the plurality of dimples of the first surface pattern and of the second surface pattern comprises semi-spheres.

13. The implantable device of claim 10, wherein the first surface pattern comprises macro sized features and the second surface pattern comprises micro sized features.

14. The implantable device of claim 10, wherein the first surface pattern comprises macro sized features, the second surface pattern comprises micro sized features, and the third surface pattern comprises nano sized features.

15. The implantable device of claim 10, wherein the macro sized features have a macro size Rz of 50 µm to 200 µm and a roughness Ra of 10 µm to 30 µm, the micro sized features have a micro size Rz of 500 nm to 20 µm and a roughness Ra of 5 µm to 10 µm, and the nano sized features have a nano size Rz of 200 nm to 500 nm and a roughness Ra of 0.5 µm to 5 µm.

16. The implantable device of claim 10, wherein the body comprises titanium or an alloy thereof.

17. The implantable device of claim 10, wherein the surface topography is substantially uniform across the top surface, the bottom surface, or both the top and bottom surfaces.

18. The implantable device of claim 10, wherein the first and second surface patterns stabilize the body when the top surface, bottom surface, or both the top and bottom surfaces contact bone.

* * * * *